(12) United States Patent  
Kiang

(10) Patent No.: US 7,112,315 B2  
(45) Date of Patent: *Sep. 26, 2006

(54) MOLECULAR NANOWIRES FROM SINGLE WALLED CARBON NANOTUBES

(75) Inventor: Ching-Hwa Kiang, Los Angeles, CA (US)

(73) Assignee: The Regents of the University of California, Oakland, CA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/354,531

(22) Filed: Jul. 15, 1999

(65) Prior Publication Data

US 2001/0051367 A1    Dec. 13, 2001

Related U.S. Application Data

(60) Provisional application No. 60/129,312, filed on Apr. 14, 1999.

(51) Int. Cl.  
*D01F 9/12* (2006.01)  
*C01N 11/04* (2006.01)

(52) U.S. Cl. .................. 423/447.1; 435/182; 997/702; 997/705; 997/750; 997/762

(58) Field of Classification Search ................ 435/176, 435/177, 180, 182  
See application file for complete search history.

(56) References Cited

U.S. PATENT DOCUMENTS

| 5,424,054 A | | 6/1995 | Bethune et al. | 423/477.2 |
|---|---|---|---|---|
| 5,457,343 A | * | 10/1995 | Ajayan et al. | 257/734 |
| 5,547,748 A | | 8/1996 | Ruoff et al. | 428/323 |
| 6,090,363 A | * | 7/2000 | Green et al. | 423/447.1 |

OTHER PUBLICATIONS

Bethune, et al., Nature, vol. 363, Jun. 17, 1993, pp. 605-607.*  
Ajayan, P.M., et al., Nature, vol. 361:333-334 (1993).  
Ajayan, P.M., et al., Nature, vol. 362:522-525 (1993).  
Dujardin, E., et al., "Capillarity and Wetting of Carbon Nanotubes, Science", vol. 265:1850-1852 (1994).  
Seraphin, S., et al., Nature, vol. 362:503 (1993).  
Ajayan, P.M., et al., Phys. Rev. Lett., vol. 72:1722-1725 (1994).  
Subramoney, S., et al., Carbon, vol. 32:507-513 (1994).  
Guerret-Piecourt, C., et al., "Relation between metal electronic structure and morphology of metal compounds inside carbon nanotubes", Nature, vol. 372:761-765 (1994).  
Wong, S.S., et al., "Covalently functionalized nanotubes as nanometre-sized probes in chemistry and biology," Nature, vol. 394:52-55 (1998).  
Kiang, C.-H., et al., J. Phys. Chem. Solids, vol. 57:35-39 (1995).  
Kiang, C.-H., et al., J. Phys. Chem., vol. 98: 6612-6618 (1994).  
Kiang, C.-H., et al., Carbon, vol. 33: 903-914 (1995).  
Kiang, C.-H., et al., Chem. Phys. Lett., vol. 259:41-47 (1996).  
Dillon, A.C., et al., "Storage of hydrogen in single-walled carbon nanotubes", Nature, vol. 386:377-379 (1997).  
Sloan, J., et al., The opening and filling of single walled carbon nanotubes (SWTs), Chem. Commun., vol. 3: 347-348 (1998).  
Service, R.F., "Superstrong Nanotubes Show They Are Smart, Too", Science, vol. 281:940-942 (1998).  
Wu, C.-G., et al., Science, vol. 364:1757 (1994).  
Kim, E., et al., Nature, vol. 376:581 (1995).  
Swager, T.M., Acc. Chem. Res. vol. 31:201 (1998).  
Pederson, M.R., et al., "Nanocapillarity in fullerene tubules," Phys. Rev Lett. vol. 69:2689-2692 (1992).  
Ebbeson, T.W., et al., "Large-scale synthesis of Carbon Nanotubes," Nature, vol. 358:220-221 (1992).  
Kiang, C.-H., et al., "Structural modification of single-layer carbon nanotubes with an electron beam," J. Phys. Chem., vol. 100:3749-3752 (1996).  
Cheng, et al., "Large-scale and low-cost synthesis of single-walled carbon nanotubes by the catalytic pyrolysis of hydrocarbons", Appl. Phys. Lett., vol. 72:3282-3284 (1998).  
Tsang, S.C., et al., "A simple chemical method of opening and filling carbon nanotubes", Nature, vol. 372:159-162 (1994).  
Chu, A., et al., "Filling of carbon nanotubes with silver, gold, and gold chloride", Chem. Mater., vol. 8:2751-2754 (1996).  
Davis, J.J., et al., "The immobilisation of proteins in carbon nanotubes", Inorganica Chimica Acta, vol. 272:261-266 (1998).

\* cited by examiner

*Primary Examiner*—David M. Naff  
(74) *Attorney, Agent, or Firm*—Berliner & Associates

(57) ABSTRACT

Unique single walled nanotube compositions and methods for making the composition wherein the nanotubes encloses foreign material capable of forming thread-like material having a solid form at ambient temperatures and pressures.

2 Claims, 2 Drawing Sheets

MOLECULAR NANOWIRES FROM SINGLE WALLED CARBON NANOTUBES

CROSS-REFERENCE WITH RELATED APPLICATIONS

This application claims the benefit of U.S. Provisional Application No. 60/129,312, filed Apr. 14, 1999.

BACKGROUND OF THE INVENTION

1. Field of the Invention

The invention relates generally to carbon nanotubes enclosing a foreign material.

2. Description of Related Art

Fullerenes are a family of closed caged molecules formed entirely of carbon in the $sp^2$-hybridized state and constitute the third form of carbon after diamond and graphite. These spherical, cavity containing molecules and their allotropes have been found to possess novel, remarkable properties, and the buckminster fullerene $C_{60}$ has been widely investigated.

In 1991 Sumio Iijima synthesized new carbon structures in the form of needlelike tubes with multiple concentric cylindrical shells of hexagonally bonded carbon atoms. These extended fullerene tube structures have been called carbon nanotubes, more specifically multiwalled nanotubes (MWNTs). These MWNTs have typical outside diameters from a few to several tens of nanometers.

It has been reported that foreign materials, other than carbon have been encapsulated or introduced into MWNTs, such as metals, semiconductors, superconductors, magnetic materials, alkali metals, gases, and organic molecules. Ajayan, P. M., et al., have reported that only a very small fraction of the MWNTs (about 1%) enclosed foreign materials [Nature, Vol. 361:333–334 (1993)]. In a companion paper, they reported the introduction of bismuth oxide into MWNTs [Ajayan, P. M., et al., Nature, Vol. 362:522–525 (1993)]. U.S. Pat. No. 5,547,748 discloses a multi-walled carbon nanotube of between 5 nm and 1000 nm encapsulating metals from the actinide or lanthanide series, paramagnetic or ferromagnetic elements, and metal alloys. Dujardin et al have described wetting and filling MWNTs with substances having low surface tension, such as sulfur, selenium, and cesium, with an upper limit to this tension of less than 200 millinewtons per meter [Dujardin, E., et al., "Capillarity and Wetting of Carbon Nanotubes, Science", Vol. 265:1850–1852 (1994)]. Compounds of yttrium [Seraphin. S., et al., Nature, Vol. 362:503 (1993)], manganese [Ajayan, P. M., et al., Phys. Rev. Lett., Vol. 72:1722–1725 (1994)], and gadolinium [Subramoney, S., et al., Carbon, Vol. 32:507–513 (1994)] were encapsulated in MWNTs. It has been reported that oxides of nickel, cobalt, iron, and uranium can be encapsulated by opening MWNTs and depositing the filling material by wet chemical techniques [Tsang, S. C., et al., Nature, Vol. 372:159–162 (1994)]. MWNTs have been filled with silver, gold, and gold chloride [Chu, A., et al., Chem. Mater, Vol. 8:2751–2754 (1996)]. MWNTs were filled with Cr, Ni, Dy, Yb, and Gd, and particles of Pd, Fe, Co and Ni have been encapsulated within nanotubes [Guerret-Piecourt, C., et al., "Relation between metal electronic structure and morphology of metal compounds inside carbon nanotubes", Nature, Vol. 372: 761–765 (1994)]. MWNTs can be created with acidic functionality, with basic or hydrophobic functionality, or with biomolecular probes at the open tip ends of the MWNTs [Wong, S. S., et al., "Covalently functionalized nanotubes as nanometer-sized probes in chemistry and biology," Nature, Vol. 394:52–55 (1998)]. Proteins and enzymes can be immobilized on the inner surfaces of MWNTs [Davis, J. J., et al., Inorganica Chimica Acta, Vol. 272:261–266 (1998)].

In 1993 it was discovered that the use of transition metal catalysts during arc discharge produced single walled nanotubes (SWNTS) [Bethune, D. S., et al., Nature, Vol. 363: 605–607 (1993), Iijima, S., et al., Nature, Vol. 363: 603–605 (1993)]. Kiang, C -H et al described the synthesis of SWNTs with a metal catalyst [Kiang, C. -H., et al., J. Phys. Chem. Solids, Vol. 57:35–39 (1995); Kiang, C. -H., et al., J. Phys. Chem., Vol. 98: 6612–6618 (1994); Kiang, C. -H., et al., Carbon, Vol. 33: 903–914 (1995); Kiang, C. -H., et al., Chem. Phys. Lett., Vol. 259:41–47 (1996)].

SWNTs are generated by arc-evaporation, by laser-vaporization of metal-doped graphite, by thinning of MWNTs using $CO_2$ by pyrolysis of the hydrocarbon, and by chemical vapor deposition. It has been reported that hydrogen gas can condense inside SWNTs [Dillon, A. C., et al., "Storage of hydrogen in single-walled carbon nanotubes", Nature, Vol. 386:377–379 (1997)]. It has also been reported that elongated crystallites of Ru were encapsulated in SWNTs [Sloan, J., et al., The opening and filling of single walled carbon nanotubes (SWTs), Chem. Commun., Vol. 3: 347–348 (1998)]. SWNTs exhibit both a smaller range of diameter and far fewer defects than MWNTs [Service, R. F., "Superstrong Nanotubes Show They Are Smart, Too", Science, Vol. 281:940–942 (1998); Sloan, J., et al., supra].

Nanotubes are superstrong and light, and can act as both conductor or semiconductor depending on the diameter and chirality of the hexagonal carbon lattice along the length of the nanotube [Dekker, C., "Carbon Nanotubes as Molecular Quantum Wires", Physics Today, Vol. 52: 22–28 (1999), Ebbeson, T. W., "Carbon Nanotubes", Physics Today, Vol. 49:26–32 (June 1996)]. Molecular electronics and nanoscale molecular surgery are but a few of the applications requiring strong, stable, small diameter nanotubes that enclose foreign materials that are capable of forming a thread-like structure having a solid form at ambient temperatures and pressures and that have few defects.

BRIEF SUMMARY OF THE INVENTION

The present invention is directed to filled SWNTs, carbon nanotubes, each comprised of a single layer of carbon atoms having an internal cavity, defined by an internal surface of the single layer of carbon atoms, and enclosing a foreign material in the internal cavity capable of forming a thread-like material having a solid form at ambient temperatures and pressures. The filled SWNTs of this invention are more stable than unfilled nanotubes because without the filled core the mechanical and/or electrical properties of the SWNTs are more sensitive to defects. Because of higher density and greater rigidity, filled SWNTs are more easily separated from the reaction debris than unfilled SWNTs. Filled SWNTs thus have the advantages of a narrow size distribution and thermal, mechanical, electrical and chemical stability.

The filled SWNTs have novel electrical, superconducting, optical, and magnetic properties. Gallium nitride nanorods have promising applications for blue and ultraviolet optoelectronic devices, for example, high-efficiency blue light-emitting diodes; See, Han, S., et al., Science, Vol. 277:1287 (1997). Organic dye in Zeolite micropores—microlasers, is one of a growing class of optically excited organic lasers that may one day replace the dye lasers, and may find novel applications in optical sensing and communication, and in consumer devices such as printers and scanners; See, Vietze, U., et al., "Zeolite-Dye Microlasers", Phys. Rev. Lett., Vol. 81:4628–4631 (1998). Arrays of bismuth nanowires have novel magnetorisistance property. Bismuth nanowires may be a degenerately doped semiconductor; See, Heremans, J., et al., "Magnetoresistance of bismuth nanowire arrays: A possible transition form one-dimensional to three-dimensional localization," Phys. Rev. B 58: R10091 (1998). SWNTs can also serve as quantum dots.

In one embodiment of the invention, atoms and molecules in either gaseous, liquid, or solid phase, and capable of forming a molecular nanowire, i.e., a thread-like material having a solid form at ambient temperatures and pressures, are introduced into SWNTs to form stable thread-like solid, structures within the SWNTs. A number of methods for introducing the foreign material into SWNTs can be used, including heating simultanous with or subsequent to arc forming of the tubes, or, in a preferred embodiment, solution phase chemistry is used to introduce the foreign material into the SWNTs, since many molecules can be introduced into solution for subsequent adsorption into nanotubes. It is roughly estimated that more than 30% of the SWNTs fill by this method. In another embodiment of the invention, the adsorption of molecules in SWNTs is influenced by an applied potential.

In accordance with this invention, a material is provided comprising an elongate metal wire of nanometer dimensions having a substantially constant diameter between about 0.7 nm and about 7 nm.

The importance of small diameter nanotubes having few defects makes these filled SWNTs amenable to a wide variety of applications such as molecular electronics [Tans, S. J., et al., "Room-temperature transistor based on a single carbon nanotube", Nature, Vol. 393: 49–52 (1998)], hydrogen storage media [Dillon, A.C., et al., "Storage of hydrogen in single-walled carbon nanotubes", Nature, Vol. 386: 377–379 (1997)], and scanning probe microscope tips [Wong, S. S., et at., "Covalently functionalized nanotubes as nanometer-sized probes in chemistry and biology," Nature, Vol. 394: 52–55 (1998)]. SWNTs can be created with acidic functionality or with basic or hydrophobic functionality, or with biomolecular probes at the open tip ends. Macroapplications include light, strong wires, batteries, fuel cells, or bulletproof vests. Biological applications include an open-ended nanotube that could inject a few molecules into a specific region of a cell to carry out molecular surgery on nucleic acids [Yakobson, B., et al., "Fullerene Nanotubes: $C_{1,000,000}$ and Beyond," American Scientist, Vol. 85: 324–337 (1997)].

These and other features, aspects, and advantages of the present invention will become better understood with regard to the following detailed description, appended claims, and accompanying drawings.

BRIEF DESCRIPTION OF THE DRAWINGS

in FIG. 2a the nanotube is free standing and open-ended.

DETAILED DESCRIPTION OF THE INVENTION

Figure 1:
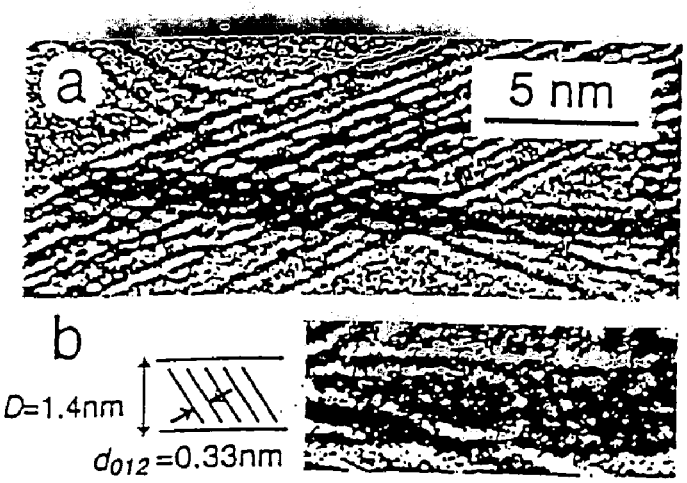
FIG. 1a shows a high resolution transmission electron micrograph (HRTEM) of a single walled carbon nanotube filled with a single-crystal bismuth nanowire.
FIG. 1b is a magnification of a portion of the HRTEM of FIG. 1a, showing lattice spacing corresponding to a bulk bismuth crystal.

As used in this invention, "foreign material" is meant to comprise materials other than carbon that are capable of forming a thread-like structure, and includes metals and organic materials. Elements that can be used in the method of Example 1, described below, are Cr, Fe, Co, Ni, Pd, Gd, Dy, Yb, Se, S, Sb, and Ge; See, Guerret-Piecourt, C., et al., "Relation between metal electronic structure and morphology of metal compounds inside carbon nanotubes," Nature, Vol. 372:761–765 (1995). Metals that can be used in the solution chemistry method of Example 3, described below, are Bi, Pb, Cd, Ga, Li, In, Rb, Zn, and Sn.

Encapsulating a single protein could also be useful. Organic materials that can be used are those that are capable of forming a thread-like material having a solid form at ambient temperatures and pressures enclosed in the internal cavity of the SWNT. Examples are such biologically active materials as proteins and enzymes, as well as polymer-forming materials. Conjugated polymers, such as polyaniline [See Wu, C. -G., et al., Science, Vol. 364:1757 (1994)]; low viscosity polymers, such as poly(methyl-methacrylate) [See Kim, E., et al., Nature, Vol. 376:581 (1995)]; and polyacetylene [See Swager, T. M., Acc. Chem. Res. Vol. 31:201 (1998)] and other organic materials useful in the form of nano-size solid threads.

Bonding between the enclosed foreign materials and the highly curved, nearly one dimensional SWNT inner surface can be significantly different from bonding to graphite basal surfaces. Therefore, a range of absorption energies of atomic and molecular species to the inner surface of SWNTs can be expected, depending on the nanotube diameter [Pederson, M. R., et al., "Nanocapillarity in fullerene tubules," Phys. Rev Lett. Vol. 69:2689–2692 (1992), Dujardin, E., et al., "Capillarity and wetting of carbon nanotubes," Science, Vol. 265:1850–1852 (1994), Guerret-Piecourt, C., et al., supra].

Because carbon nanotubes are capped at their ends by pentagons, [Ebbeson, T. W., et al., "Large-scale synthesis of Carbon Nanotubes," Nature, Vol. 358:220–221 (1992)], in order to allow for better filling, the capped SWNTs can be opened, in one embodiment, by exposing the SWNTs to a reactive gas. According to the present invention the introduction of the foreign material into the SWNTs can be accomplished either simultaneously with formation of the SWNT or after the opening of the capped end or ends of the SWNT. In another embodiment, sufficient heat may be applied to the capped SWNT so as to open ends of the SWNT [Kiang, C. -H., et al., "Structural modification of single-layer carbon nanotubes with an electron beam," J. Phys. Chem., Vol. 100:3749–3752 (1996)]. In still another embodiment, the capped end of the SWNT may be exposed to a reactive liquid (a strong acid such as HCl or $HNO_3$ or a strong base such as ammonia) in order to open the SWNT.

In the following examples, high-resolution transmission electron microscopy (HRTEM) studies were carried out on the synthesized samples. The studies were done on Phillips CM200 and CM300 microscopes equipped with Gatan slow scan camera and image filter.

EXAMPLE 1

The cobalt-catalyzed preparation of carbon nanotubes by arc discharge is described in U.S. Pat. No. 5,424,054, the description thereof being incorporated herein by reference. In this example, bismuth was vaporized along with cobalt and graphite powder via the arc discharge method. The addition of bismuth as a co-catalyst and as a source for filling SWNTs presents a unique method and results in a composition different from that disclosed in U.S. Pat. No. 5,424,054. The arc discharge method involved contacting carbon vapor with a transition metal vapor and with the foreign material vapor, preferably in an inert atmosphere. Carbon vapor shall mean a gas of carbon atoms, ions or clusters. The carbon vapor can be conveniently produced by thermally vaporizing solid carbon. Suitable forms of solid carbon are amorphous carbon, hydrocarbon, graphite, coal, activated or decolorizing carbon or mixtures thereof. The solid carbon can be vaporized by heating carbon using a variety of heating techniques such as electric arc heating, RF induction heating, laser heating, electron beam heating, RF plasma heating or plasma-spray heating. Other heating techniques, such as, heating with an oven or using heat generated from chemical reactions, will be known by those skilled in the art; see Cheng, et al., "Large-scale and low-cost synthesis of single-walled carbon nanotubes by the catalytic pyrolysis of hydrocarbons", Appl. Phys. Lett., Vol. 72:3282–3284 (1998). Preferably, the solid carbon is vaporized by electric-arc heating. Preferably, solid carbon in the form of a graphite rod is used as one of the two electrodes in the electric-arc heating process.

The synthesis was carried out in an arc discharge chamber. The electrodes used were 6 mm diameter graphite rods, with the anode containing mixtures of, in atomic percentage, graphite powder (90%), cobalt catalyst (5%), and bismuth co-catalyst (5%). Bismuth was used to improve the catalytic properties of the primary catalyst for producing high-yield, large diameter SWNTs and as a source material for filling the nanotubes. An electric arc, running a DC current at 95 A under 400 Torr helium, vaporized the carbon, the cobalt catalyst, and the bismuth metal incorporated into the composite anode. Incorporation was done by drilling into the anode and filling the hole with the graphite, bismuth, and cobalt powders. In place of powders of metal, one can use metal oxides or other metal compounds.

RESULTS OF EXAMPLE 1

FIGS. 1a and 1b are HRTEMs of a 1.4 nm diameter SWNT entirely filled with a single crystal bismuth nanowire. The filling of the SWNT extended throughout the entire stretch of the nanotube (FIG. 1a). A SWNT, entirely filled with a single crystal of bismuth of 1 nm inner diameter and 30 nm in length, was synthesized (FIG. 1b).

This method produced 20 grams per hour of raw soot with a high content of SWNTs, greater than about 30%. The nanotube diameter distribution was measured from HRTEM images, which showed the SWNTs had diameters between about 0.7 nm to about 2 nm, 15% had diameters between about 2 nm to about 7 nm, and 15% had diameters between about 3 nm to about 7 nm.

The filling of the SWNTs with bismuth metal occurred during the high temperature, estimated to be about 1,000° C., gas phase reaction when the bismuth metal incorporated into the composite anode was vaporized with carbon and cobalt in the helium atmosphere. While less than 1% of the SWNTs were filled with this method, perhaps due to transport limitations, the extent of filling in a given nanotube suggested a strong capillary attraction for bismuth in small diameter SWNTs.

EXAMPLE 2

Solid state bismuth metal was used as a starting material and was introduced into SWNT by heating. Since SWNTs can be opened by heating (FIG. 2a), nanotube soot was prepared with excess about 5 atomic % bismuth nanoparticle deposits, the soot was heated in air at a rate of 20° C. per minute to raise the temperature to 400° C., and was kept at 400° C. for 30 minutes under about 1 atmosphere.

RESULTS OF EXAMPLE 2

Figure 2:
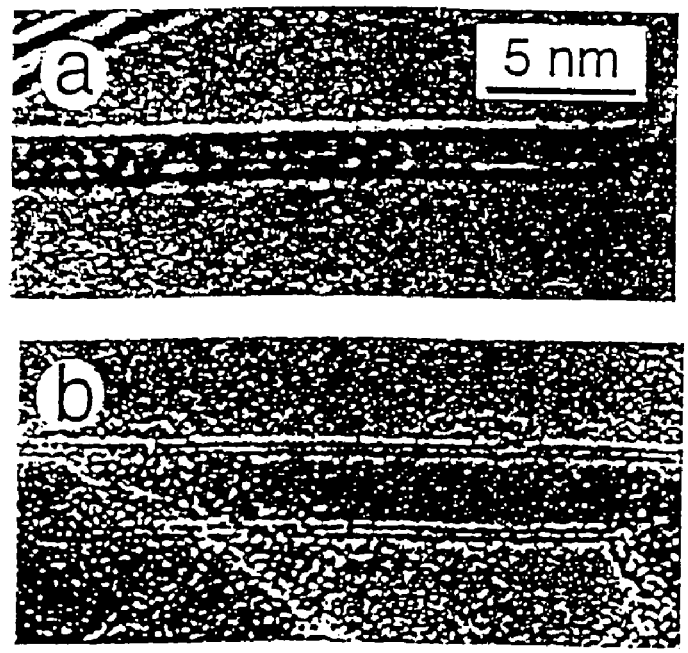
FIGS. 2a and 2b are HRTEMs of filled single walled carbon nanotubes, where the internal cavities of the nanotibe are filled with amorphous carbon (FIG. 2a) or bismuth (FIG. 2b)
Figure 3:
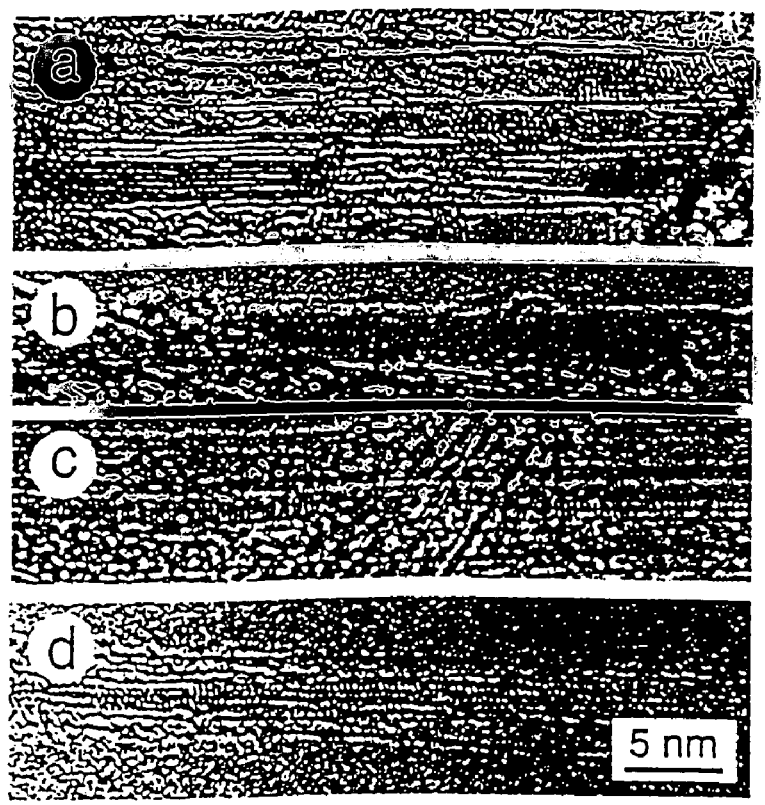
FIGS. 3a to 3d are HRTEMs of single walled carbon nanotubes filled by means of an efficient solution chemistry technique, showing: a single bismuth crystal with lattice spacing of 0.328 (FIG. 3a), bismuth crystals in a 3 nm diameter nanotube (FIG. 3b), bismuth in a nanotube of about 1 nm (FIG. 3c), and atoms of bismuth arranged in columns inside the single walled nanotubes (FIG. 3d).

FIGS. 2a and b are HRTEMs of the SWNTs after heat treatment. A 1.6 nm diameter SWNT was opened by heating, providing opportunity for filling and functionalization. The material inside the nanotube was amorphous carbon, perhaps due to the short annealing time (FIG. 2a). Bismuth was drawn into a SWNT by heating in air at 400° C. This process resulted in the addition of a second protective layer of carbon around the filled SWNT, giving improved stability and providing better isolation of an individual nanotube. The second layer was formed during the heating process, since the starting materials are exclusively single layered (FIG. 3b).

About 10% of the nanotubes were filled with this method, compared to the 1% that can be achieved for MWNTs. Most of the metal nanotubes were longer than tens of nanometers. About 20% of these filled SWNTs had a protective carbon layer deposited on them (FIG. 3b). The SWNT diameter is about 1–3 nm and is unlike MWNTs which typically have 2–50 layers and a diameter of 2–50 nm.

EXAMPLE 3

Bismuth was introduced into the SWNT using solution phase chemistry, a more general route that allows functionalizing carbon nanotubes with a variety of molecules. SWNT soot was stirred in concentrated HCl for 7.5 hours at room temperature in order to remove excess metal particles. The solution was centrifuged for 10 minutes and the precipitate was then dried, washed with deionized water, and dried again. After 2 wash cycles, the solution was removed and the sample was dried at 70° C. overnight and two wash cycles were repeated. To fill the SWNT, the SWNT soot sample was stirred in 1M of $Bi(NO_3)_3$ in $HNO_3$ solution. The $HNO_3$ was used to open the capped ends of the SWNT. After centrifugation, the precipitate was washed, dried and heated in a $H_2$ flow in an oven where the temperature was raised at 5° C. per minute and kept at 350° C. for 3 hours with a 15 minute cool down period. The sample was then washed and dried overnight at 60° C.

RESULTS OF EXAMPLE 3

FIGS. 3a to 3d are HRTEMs of SWNTs filled by the technique of solution phase chemistry. More than 30% of the SWNTs were filled by this method. Most of the fillings are single bismuth crystals, as determined by X-ray (EDX) analysis. The diameter of the crystal is the same as the inner diameter of the SWNTs. The lengths of filling range from several tens of nanometers to hundreds of nanometers, with many of the tubes nearly filled, which suggests a strong interaction between the inner surface of the nanotube and the metal atoms. The lattice fringes can be seen clearly throughout the tube filling, with smaller diameter nanotubes showing individual atoms arranged in columns of bismuth nanowires. FIG. 3a shows a single bismuth crystal inside the nanotube. The most commonly observed lattice spacing is $d_{012}$=0.33 nm. The bottom nanotube in FIG. 3a has the (012) lattice fringes perpendicular to the tube axis and the spacing can be determined to high accuracy. The spacing is 0.328 nm, the same as in the bulk bismuth metal. Other lattice spacings were observed that deviate from the lattice spacings of bulk bismuth crystal by about 5%. One can observe on occasion (003) lattice fringes with spacings of 0.395 nm or (101) lattice fringes with spacings of 0.374 nm. Analogous size effects have been observed in the crystalline structure of small diameter MWNTs [Kiang, C. -H., et al., Size effects in carbon nanotubes, Phys. Rev. Lett., Vol. 81:1869–1872 (1998)].

Referring to FIG. 3b, a nanotube with a 3 nm diameter had crystalline bismuth filling with a structure similar to that of bulk bismuth crystals. As shown in FIG. 3c, the d spacing of the bismuth crystals in small diameter nanotubes (D~1 nm) differs from that of bulk bismuth crystal. FIG. 3d shows atoms of bismuth arranged in columns inside SWNTs. There are two to three columns of bismuth nanowires inside each nanotube, indicating that the nanowire is composed of approximately five atoms in the plane perpendicular to the tube axis.

Figure 4:
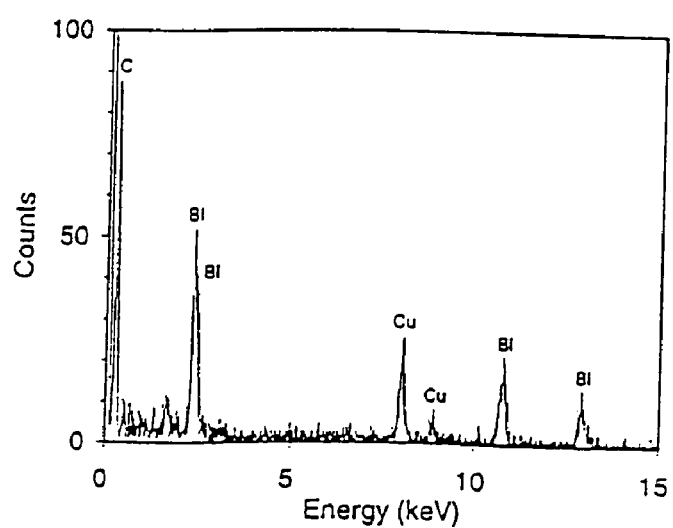
FIG. 4 shows an energy dispersive X-ray spectrum of bismuth filled nanotubes.

FIG. 4 is an energy of dispersed X-ray (EDX) spectrum of filled tubes which shows strong peaks arising from the $K_\alpha$, $K_\beta$, $L_\alpha$, and $L_\beta$ transitions of bismuth. The peak from carbon is from the SWNT and the weaker peaks from Cu are from the transmission electron microscope specimen support grid.

Most of the filling of the SWNTs was crystalline with a very high aspect ratio, unlike the particle-like fillings observed inside MWNTs [Tsang, S. C., et al., "A simple chemical method of opening and filling carbon nanotubes", Nature, Vol. 372:159–162 (1994), Chu, A., et al., "Filling of carbon nanotubes with silver, gold, and gold chloride", Chem. Mater., Vol. 8:2751–2754 (1996)]. This suggests that a strong capillary force, stronger than in MWNTs, is responsible for efficient filling of SWNTs [Ajayan, P. M., et al., supra]. The strong capillary effect in SWNTs should allow them to host a wide variety of nanoscale materials. The results indicate the tendency for molecules to be drawn into nanotubes in either crystalline or amorphous phases, demonstrating the feasibility of filling SWNTs using solid or gas phase molecules.

EXAMPLE 4

The procedures of Davis, et al., "The immobilisation of proteins in carbon nanotubes", Inorganica Chimica Acta, Vol. 272:261–266 (1998), for filling MWNTs with a protein or enzyme, can be followed to fill SWNTs with Metallothionein. A SWNT sample can be prepared and opened, according to the procedures described in EXAMPLE 1 to 3 above.

2 mg of freshly opened SWNTs can be mixed with 0.5 mg metallothionein (MT) II (MW 7 kDa) in 1 ml deionized water. The flask contents are left to stand at room temperature without stirring and a constant stream of nitrogen is maintained over the surface of the suspension/solution in order to aid evaporation. When most of the water has evaporated (3 days) the flask can be placed in a vacuum desiccator over $P_2O_5$ for three days before transmission electron microscopy (TEM) examination.

EXAMPLE 5 TO 6

The procedures of EXAMPLE 4 can be followed to open and fill SWNTs with cytochrome c (Horse heart, MW 12.4 kDa) and cytochrome $c_3$ (Desulfovibrio vulgaris, MW 14 kDa).

EXAMPLE 7

The procedures of Davis, et al., supra, for filling MWNTs with a protein or enzyme, can be followed to fill SWNTs with β-lactamase I. A SWNT sample can be prepared and opened, according to the procedures described in EXAMPLE 1 to 3 above.

Purified β-lactamase I (Bacillus cereus 569H/9 MW 29 kDa) is dissolved in 1 ml deionised water (3.8 m) and 20 mg freshly oxidised, washed and dried carbon SWNTs are added. The solution/suspension can be left to stand for 3 h and the water is then removed.

EXAMPLES 8 to 11

The procedures of Example 3 can be followed by substituting the following metals for bismuth, mutatis mutandis: Ni, Pb, Pd, and Mn.

The filled SWNTs are useful in molecular electronics such as a room-temperature transistor, see Tans, S. J., et al., "Room-temperature transistor based on a single carbon nanotube," Nature, Vol. 393: 49–52 (1998). SWNTs can also by used as scanning probe microscope tips, created with acidic, basic or hydrophobic functionalities, or created with biomolecular probes at the open tip ends; see Wong, S. S., et al, "Covalently functionalized nanotubes as nanometer-sized probes in chemistry and biology," Nature, Vol. 394: 52–55 (1998). An open-ended SWNT could also be used to carry out molecular surgery on nucleic acids, see Yakobson, B., et al., "Fullerene Nanotubes: $C_{1,000000}$ and Beyond," American Scientist, Vol 85: 324–337(1997).

The following references are incorporated herein by reference: Ajayan, P. M., et al., Nature, Vol. 361:333–334 (1993); Ajayan, P. M., et al., Nature, Vol. 362:522–525 (1993); U.S. Pat. No. 5,547,748; Dujardin, E., et al., Science, Vol. 265:1850–1852 (1994); Seraphin. S., et al., Nature, 362: 503 (1993); Ajayan, P. M., et al., Phys. Rev. Lett., 72:1722–1725 (1994); Subramoney, S., et al., Carbon, 32:507–513 (1994); Tsang, S. C., et al., Nature, 372:159–162 (1994); Chu, A., et al., Chem. Mater, Vol. 8:2751–2754 (1996); Guerret-Piecourt, C., et al., Nature, Vol. 372:761–765 (1994); Wong, S. S., et al., Nature, Vol. 394:52–55 (1998); Davis, J. J., et al., Inorganica Chimica Acta, Vol. 272:261–266 (1998); Bethune, D. S., et al., Nature, Vol. 363:605–607 (1993); Iijima, S., et al., Nature, Vol. 363: 603–605 (1993); Kiang, C. -H., et al., J. Phys. Chem. Solids, Vol. 57:35–39 (1995); Kiang, C. -H., et al., J. Phys. Chem., Vol.98: 6612–6618 (1994); Kiang, C. -H., et al., Carbon, Vol. 33: 903–914 (1995); Kiang, C. -H., et al., Chem. Phys. Lett., Vol.259:41–47 (1996); Dillon, A. C., et al., Nature, Vol. 386:377–379 (1997); Sloan, J., et al., Chem. Commun., Vol. 3: 347–348 (1998); Service, R. F., Science, Vol. 281:940–942 (1998); Dekker, C., Physics Today, Vol. 52: 22–28 (1999); Ebbeson, T. W., Physics Today, Vol. 49:26–32 (1996); Han, S., et al., Science, Vol. 277:1287 (1997); Vietze, U., et al., Phys. Rev. Lett., Vol. 81:4628–4631 (1998); Heremans, J., et al., Phys. Rev. B 58:

R10091 (1998); Tans, S. J., et al., Nature, Vol. 393: 49–52 (1998); Yakobson, B., et al., American Scientist, Vol 85: 324–337 (1997).

Although the foregoing invention has been described in some detail by way of illustration and example for purposes of clarity and understanding, it will be obvious that various modifications and changes which are within the knowledge of those skilled in the art are considered to fall within the scope of the appended claims.

The invention claimed is:

1. A method of making bismuth metal nanowire-filled single walled carbon nanotubes comprising:
   a) providing hollow single walled carbon nanotubes, each having a wall formed of a single layer of carbon atoms and having closed ends;
   b) providing bismuth metal capable of forming molecular nanowire; and
   c) heating the hollow single walled carbon nanotubes and the bismuth metal in air under atmospheric pressure at a temperature of 400° C. to open the ends of the nanotubes and introduce said bismuth metal into said single walled carbon nanotubes by capillary force to form bismuth metal nanowire therein.

2. A method of making bismuth metal nanowire-filled single walled carbon nanotubes, comprising:
   a) providing pre-formed hollow single walled carbon nanotubes, each having a wall formed of a single layer of carbon atoms and having closed ends;
   b) providing a solution of nitric acid and bismuth metal ions capable of forming a molecular nanowire having a solid form; and
   c) mixing said pre-formed hollow single walled carbon nanotubes with said solution of nitric acid and bismuth metal ions whereby the nitric acid opens the closed ends of the nanotubes and said bismuth metal ions are introduced into said pre-formed hollow single walled carbon nanotubes to form bismuth metal nanowire in more than 30% of said nanotubes.

* * * * *